(12) United States Patent
Maskin (10) Patent No.: US 12,004,997 B2
(45) Date of Patent: Jun. 11, 2024

(54) GLAND OR DUCT DIAGNOSTIC AND TREATMENT METHODS AND RELATED APPARATUS

(71) Applicant: MGD Innovations, Inc., Tampa, FL (US)

(72) Inventor: Steven L. Maskin, Tampa, FL (US)

(73) Assignee: MGD Innovations, Inc., Tampa, FL (US)

(*) Notice: Subject to any disclaimer, the term of this patent is extended or adjusted under 35 U.S.C. 154(b) by 194 days.

(21) Appl. No.: 17/466,063

(22) Filed: Sep. 3, 2021

(65) Prior Publication Data

US 2021/0393437 A1    Dec. 23, 2021

Related U.S. Application Data (60) Division of application No. 15/368,949, filed on Dec. 5, 2016, now Pat. No. 11,110,003, which is a division of application No. 12/643,333, filed on Dec. 21, 2009, now Pat. No. 9,510,844, which is a continuation-in-
(Continued)

(51) Int. Cl.
*A61F 9/007* (2006.01)
*A61B 17/22* (2006.01)
(Continued)

(52) U.S. Cl.
CPC .......... *A61F 9/00718* (2013.01); *A61B 17/22* (2013.01); *A61F 9/0008* (2013.01);
(Continued)

(58) Field of Classification Search
CPC ............... A61B 17/3207; A61F 9/0008; A61F 9/00718; A61M 25/0026; A61M 25/007
See application file for complete search history.

(56) References Cited

U.S. PATENT DOCUMENTS

| 5,486,165 A | 1/1996 | Stegmann |
| 6,142,990 A | 11/2000 | Burk |

(Continued)

FOREIGN PATENT DOCUMENTS

| JP | 11-221247 | 8/1998 |
| WO | 9404155 | 3/1994 |
| WO | 2008076544 | 6/2008 |

OTHER PUBLICATIONS

PCT International Searching Authority; International Search Report for PCT/US2008/083318 dated Jun. 11, 2009; entire document.
(Continued)

*Primary Examiner* — Deanna K Hall
(74) *Attorney, Agent, or Firm* — Allen, Dyer, Doppelt & Gilchrist, P.A.

(57) ABSTRACT

A method is provided for treating a gland or duct of a patient. In a particular embodiment, an obstruction in a gland or duct and the orifice thereof can be alleviated; in another, a substance can be injected thereinto; in yet another, the gland can be aspirated. The method includes the step of inserting an elongated probe into a gland or duct via an orifice thereinto. In some embodiments the probe can have a longitudinal lumen therethrough, with at least one distal hole through the probe wall in fluid communication with the lumen. The lumen can be used in concert with a source of suction for removing debris from the gland or duct, and/or with a source of a fluid and pumping means, for injecting a substance into the gland or duct.

5 Claims, 12 Drawing Sheets

Related U.S. Application Data part of application No. 12/305,094, filed as application No. PCT/US2008/083318 on Nov. 13, 2008, now Pat. No. 10,159,599.

(60) Provisional application No. 60/987,521, filed on Nov. 13, 2007.

(51) Int. Cl.
| | |
|---|---|
| *A61F 9/00* | (2006.01) |
| *A61M 25/00* | (2006.01) |
| *A61M 31/00* | (2006.01) |
| *A61B 17/3203* | (2006.01) |
| *A61B 17/3207* | (2006.01) |
| *A61B 90/00* | (2016.01) |
| *A61F 2/95* | (2013.01) |

(52) U.S. Cl.
CPC ...... *A61M 25/0026* (2013.01); *A61M 25/007* (2013.01); *A61M 31/00* (2013.01); *A61B 2017/22079* (2013.01); *A61B 2017/22082* (2013.01); *A61B 17/32037* (2013.01); *A61B 17/3207* (2013.01); *A61B 2090/3987* (2016.02); *A61B 2217/005* (2013.01); *A61B 2217/007* (2013.01); *A61F 2/95* (2013.01)

(56) References Cited

U.S. PATENT DOCUMENTS

| | | | |
|---|---|---|---|
| 6,344,047 B1 | 2/2002 | Price et al. | |
| 6,428,502 B1 | 8/2002 | Lang | |
| 6,936,053 B1 | 8/2005 | Weiss | |
| 7,211,070 B2 | 5/2007 | Soroudi | |
| 7,678,065 B2 | 3/2010 | Haffner | |
| 8,249,695 B2 | 8/2012 | Grenon et al. | |
| 8,491,549 B2 | 7/2013 | Conston et al. | |
| 2002/0116750 A1 | 8/2002 | Korb | |
| 2003/0072711 A1 | 4/2003 | Korb | |
| 2003/0211043 A1 | 11/2003 | Korb | |
| 2004/0237969 A1 | 12/2004 | Fuller | |
| 2006/0149194 A1* | 7/2006 | Conston | A61B 17/3421 604/294 |
| 2006/0153885 A1 | 7/2006 | Korb et al. | |
| 2007/0016254 A1 | 1/2007 | Grenon et al. | |
| 2007/0016255 A1 | 1/2007 | Korb et al. | |
| 2007/0016256 A1 | 1/2007 | Korb et al. | |
| 2007/0027431 A1 | 2/2007 | Korb et al. | |
| 2007/0036726 A1 | 11/2007 | Korb | |
| 2007/0260201 A1 | 11/2007 | Prausnitz et al. | |
| 2008/0082078 A1* | 4/2008 | Berlin | A61F 9/0017 604/521 |
| 2008/0319462 A1* | 12/2008 | Montague | A61M 25/0662 606/159 |
| 2009/0043321 A1 | 2/2009 | Conston | |

OTHER PUBLICATIONS

European Searching Authority; Supplemental European Search Report and Written Opinion dated Oct. 29, 2010; entire document.

* cited by examiner

GLAND OR DUCT DIAGNOSTIC AND TREATMENT METHODS AND RELATED APPARATUS

CROSS-REFERENCE TO RELATED APPLICATIONS

This application is a divisional of U.S. Non-provisional application Ser. No. 15/368,949, filed on Dec. 5, 2016, which is a divisional of U.S. Non-provisional application Ser. No. 12/643,333, filed on Dec. 21, 2009, which is a continuation-in-part of U.S. Non-provisional application Ser. No. 12/305,094, filed on Dec. 16, 2008, which was the § 371 National Stage of International Application No. PCT/US2008/083318, filed on Nov. 13, 2008, which claims the benefit of U.S. Provisional Application Ser. No. 60/987,521, filed on Nov. 13, 2007, the contents of which applications are hereby incorporated by reference in their entirety.

FIELD OF THE INVENTION

The present invention relates to systems, devices, and methods for treating and diagnosing ailments of glands and ducts, and particularly to removing obstructions or other types of material from, and adding material such as medication into, glands and ducts.

BACKGROUND OF THE INVENTION

There are thousands of different glands and ducts in the human body, producing a wide variety of secretions. Problems with individual glands or ducts can result in conditions that are irritating, at best, and can present potentially serious health issues. Because of the small size of most glands and ducts, diagnosing and treating problems with individuals glands or ducts can be difficult or impossible with current technology and therapeutic methods.

To give one example, "dry eye syndrome" can be caused by, among other things, obstructions in the meibomian gland, preventing lipid secretions from reaching the surface of the eye. These lipid secretions, in a healthy eye, form the outer layer of the tear film, and thereby assist in reducing tear evaporation during waking hours.

Currently, dry eye syndrome is treated, depending upon the severity, with over-the-counter preserved tears, topical and systemic medications, and even surgery. The patient's environment, dietary habits, and medications are considered and can be addressed if thought to be a factor in producing patient's dry eye syndrome.

However, at present there is no effective way of removing obstructions within the meibomian gland, and therefore it would be desirable to provide a system, device, and method for doing so. Similarly, other glands and ducts, both ophthalmic and non-ophthalmic could benefit from such systems, devices and methods.

SUMMARY OF THE INVENTION

The present invention is directed to a system, device, and method for treating an individual gland or duct of a patient. In a particular aspect, an obstruction in a gland or duct and the orifice thereof can be alleviated; in another, a substance can be injected thereinto; in yet another, the gland or duct can be aspirated.

The method comprises inserting an elongated probe into a gland or duct via an orifice thereinto. In some aspects the probe can have a longitudinal lumen therethrough, with at least one distal hole through a probe wall in fluid communication with the lumen. The lumen can be used in concert with a source of suction for removing debris from the gland or duct, and/or with a source of a fluid and pumping means, for injecting a substance into the gland or duct.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF PREFERRED EMBODIMENTS

A description of the preferred embodiments of the present invention will now be presented with reference to FIGS. 1-32.

The system, device, and method for treating a gland or duct of an eyelid of a patient can include the use of a probe to perform a plurality of procedures, such as, but not intended to be limited to, alleviating an obstruction therein. For illustrative and exemplary purposes, the following embodiments are described in the context of treatment of a meibomian gland. However, the present invention contemplates the treatment of any bodily gland or duct. For example, other ophthalmic glands or ducts that can be treated include lacrimal glands and associated secretory ducts, accessory lacrimal glands of Krause and Wolfring, and sebaceous glands of Zeis. Examples of non-ophthalmic glands or ducts that can advantageously be treated pursuant to the present invention include skin-related sebaceous and sweat glands.

Figure 1:
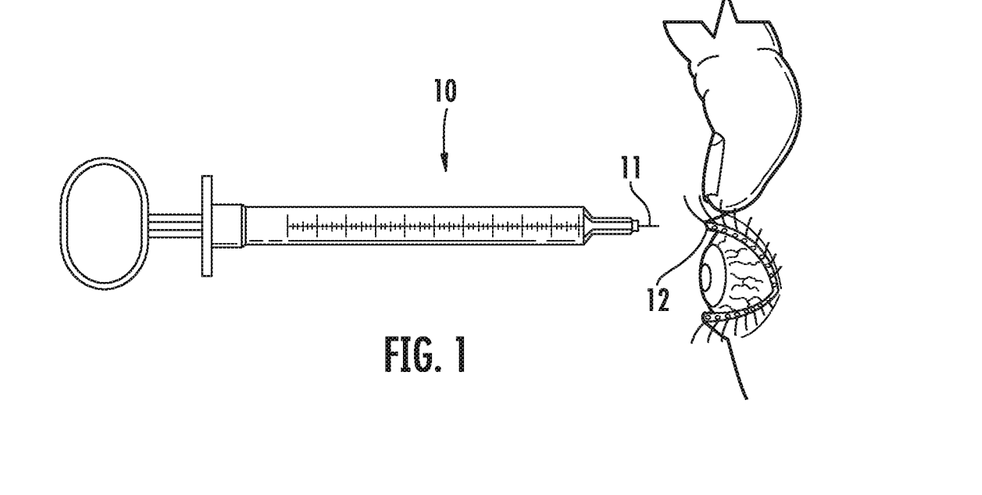
FIG. 1 is a side perspective view of a probe being inserted into a meibomian gland of an eyelid of a patient.
Figure 2:
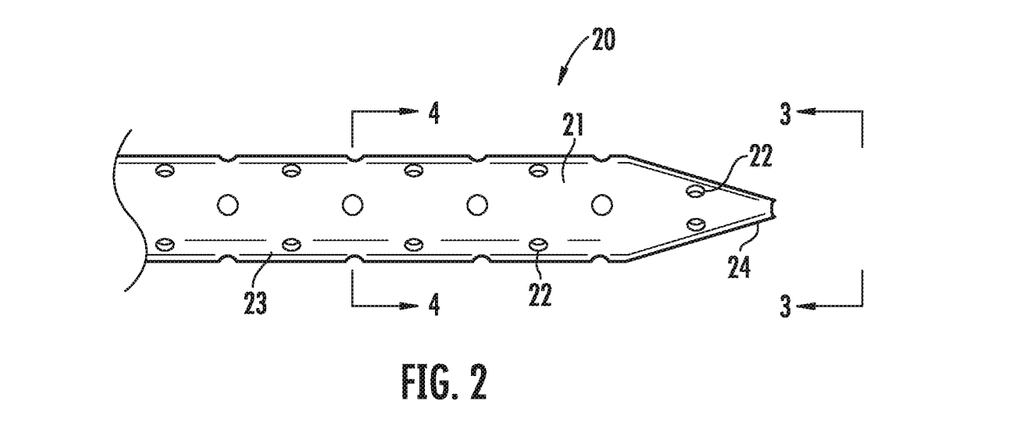
FIG. 2 is a side perspective view of a probe having apertures into a lumen.
Figure 3:
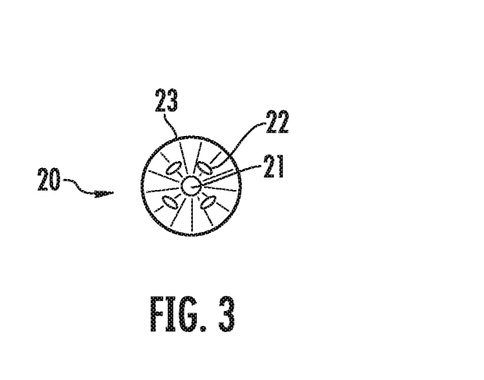
FIGS. 3 and 4 are cross-sectional views of the probe of FIG. 2 along lines 3-3 and 4-4, respectively.
Figure 4:
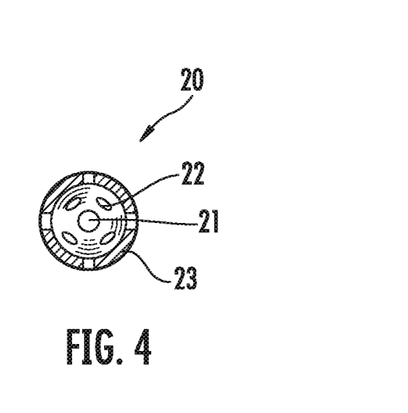
Figure 5:
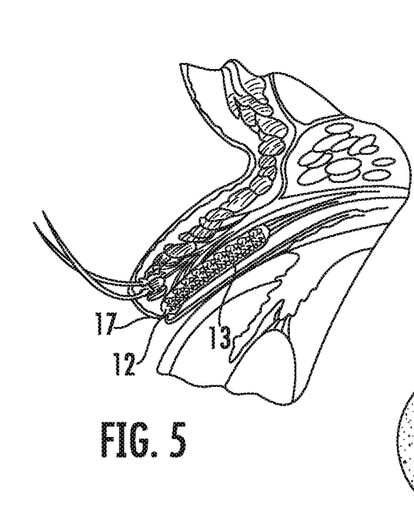
FIG. 5 is a side cross-sectional view of an eyelid, including a meibomian gland.
Figure 6:
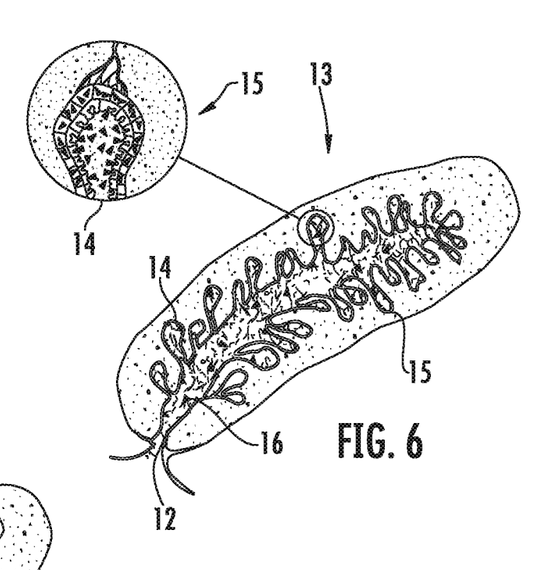
FIG. 6 is a side cross-sectional view of a meibomian gland and a detailed view of an acinar complex.
Figure 7:
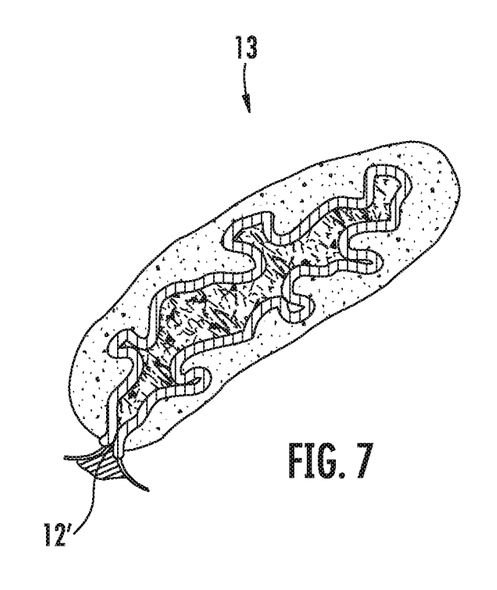
FIG. 7 is a cross-sectional view of an obstructed meibomian gland.
Figures 8, 9:
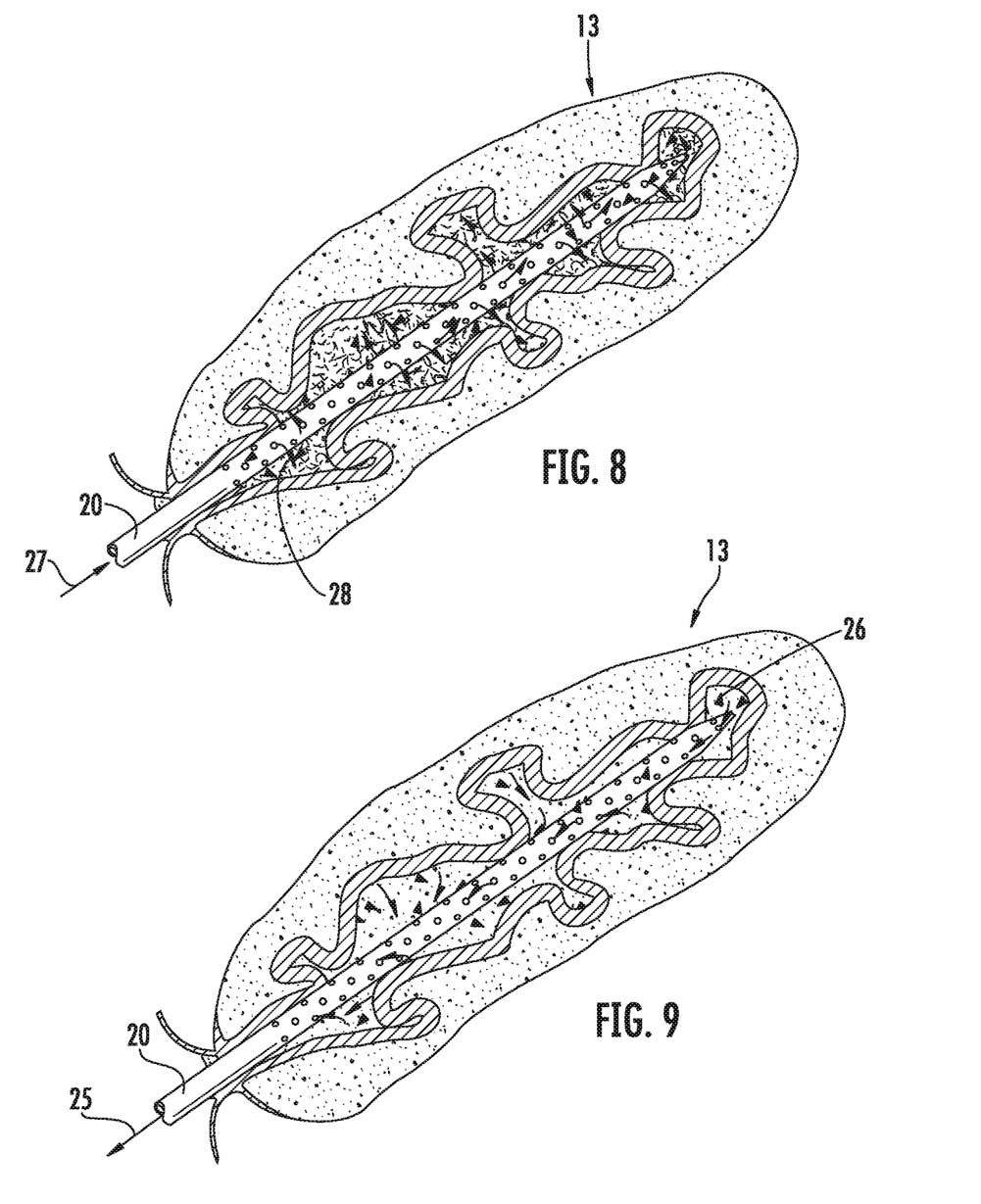
FIGS. 8 and 9 are side cross-sectional views of a meibomian gland with a probe inserted thereinto and injecting a pharmacological agent (FIG. 8) and performing aspiration (FIG. 9).

The present inventor has found that the meibomian gland can be successfully penetrated with such a probe, to clear obstructions or for other treatments, with a sufficiently thin probe. Accordingly, all embodiments entail the use of an elongated probe having a distal portion dimensioned for insertion into a meibomian gland via an orifice thereof. An exemplary probe 10 (FIG. 1) has a tip or distal end 11 dimensioned for insertion into an orifice 12 of a meibomian gland 13 (FIGS. 5-7). In basic embodiment, the distal end 11 is a thin wire fixedly secured, for instance with epoxy, to the remainder of the probe 10. The distal end 11 can be formed from stainless steel or another bio-suitable material. The probe 10 can be made to be autoclavable and re-usable, or disposable for one-time use.

The meibomian gland 13 is a modified sebaceous gland surrounded by dense collagen that produces oil droplets, waxes, and cholesterol 14 that migrate from evaginations 15 in the gland's interior space 16 toward the orifice 12 at the eyelid margin 17. The lipid secretions produced serve to stabilize tears, and there are typically approximately 24 such glands per human eyelid. An obstructed orifice 12' is illustrated in FIG. 7.

A typical gland orifice 12 has a diameter of approximately 0.1 mm. Thus, the probe 10 advantageously has distal end with an outer diameter of approximately 100 μm or less, and most advantageously approximately 50 μm to approximately 80 μm. Alternately, probes with a larger outer diameter, of between approximately 100 μm and approximately 150 μm, particularly for glands or ducts with larger orifices, but also for meibomian glands. Additionally, a typical, non-atrophied gland 13 has a depth, from the orifice 12 to a distal end 19, of approximately 4 mm to approximately 6 mm. Generally, the lower lid has shorter, wider glands than the upper lid. Thus, the probe 10 advantageously has a distal end with a length of 6 mm or less. Distal ends 11 with lengths of approximately 1 mm, approximately 2 mm and approximately 4 mm are also advantageous.

Where a wider distal end is to be inserted, for example having an outer diameter closer to 100 μm, it has been found advantageous to previously insert one or more narrower distal ends, for example, 50 μm and/or 80 μm to initially clear any blockage within the orifice 12 and to relax the orifice to ease entry of the larger distal end(s). Depending on the particular circumstances, for instance the time constraints or pain tolerance of the patient, a week or more can elapse between insertion of the narrower and wider distal ends.

Where a longer distal end is to be inserted, for example having a length of approximately 4 mm to 6 mm, it has been found advantageous to previously insert one or more shorter distal ends, for example, 1 mm or 2 mm to initially clear any blockage within the orifice 12. For distal ends of equal diameter, the shorter distal ends will generally exhibit a greater resistance to bending than the longer distal ends. Thus, the likelihood of successful insertion of longer distal ends into the meibomian glands can be enhanced with prior insertion of one or more shorter distal ends.

In practice with a probe 10, the present inventor has discovered evidence of the formation of both fibrotic bands and vascular structures with the meibomian gland central duct. The presence of fibrotic bands within the meibomian gland duct can be indicated by initial resistance to the insertion of the probe 10 that is overcome following a "pop" upon breaking through the bands. The presence of vascular structures can be indicated by the presence of a drop of blood after removing the probe 10. The routine existence of such structures within the meibomian gland duct was, to knowledge of the present inventor, previously unknown. Based on this discovery, the present invention further extends to therapeutic modalities to prevent the re-formation of such structures. Thus, treatment can be further directed at remedying the condition underlying the improper or reduced function of the meibomian gland, rather than simply clearing obstructions as they form. For instance, medicines including fibrous tissue and/or vascular tissue growth inhibiting agents, such as steroids and/or vascular endothelial growth factor (VEGF) inhibitors, can be introduced into the meibomian gland.

Subsequent to the present invention, penetration of the meibomian gland to clear obstructions has been accomplished using an instrument having an energized tip. Using plasma energy, the device effectively vaporizes obstructions, as well as any other matter, including living tissue, that comes into contact with the energized tip. Significantly, the probe 10 and related methods of use do not require the application of thermal energy, electromagnetic energy or other radiation, or other energy beyond the application of mechanical force sufficient to physically penetrate the meibomian gland. However, the present invention is not necessarily limited to purely physical penetration. Additionally, the present invention can advantageously include the application of additional energy after the probe 10 has been inserted through the orifice 12.

In addition to reducing the risk of trauma to otherwise healthy tissue, the penetration of the meibomian gland without the application of thermal or electromagnetic energy to the probe 10 facilitates the diagnosis of the potential underlying conditions described above. For instance, plasma energy would readily vaporize fibrotic bands, not allowing the surgeon to feel the indicative resistance and subsequent pop. Similarly, vascular structures would also be vaporized, and capillaries feeding the structures would likely be immediately cauterized, eliminating the blood evidence.

Figure 30:
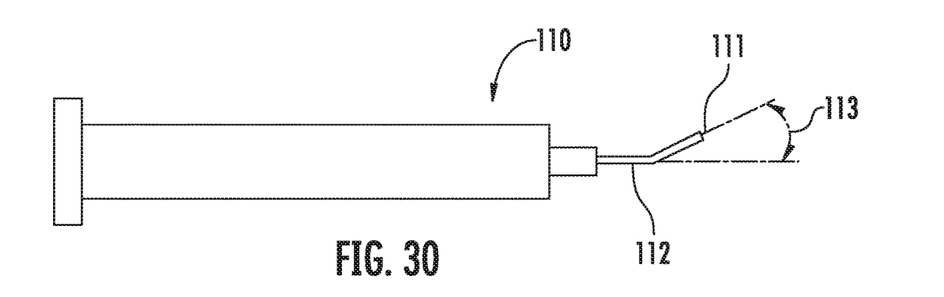
FIG. 30 is a schematic side view of a probe having a distal end connected with a bent cannula.

In another embodiment (FIG. 30), a probe 110, a distal end 111 is attached to the probe 110 by a bent cannula 112. The bent cannula 112 serves to move most of the body of the probe 110 out of the line of sight of a doctor when inserting the distal end 111 in the meibomian gland. Advantageously, the cannula is bent to an angle 113 of approximately 30 degrees.

Figure 31:
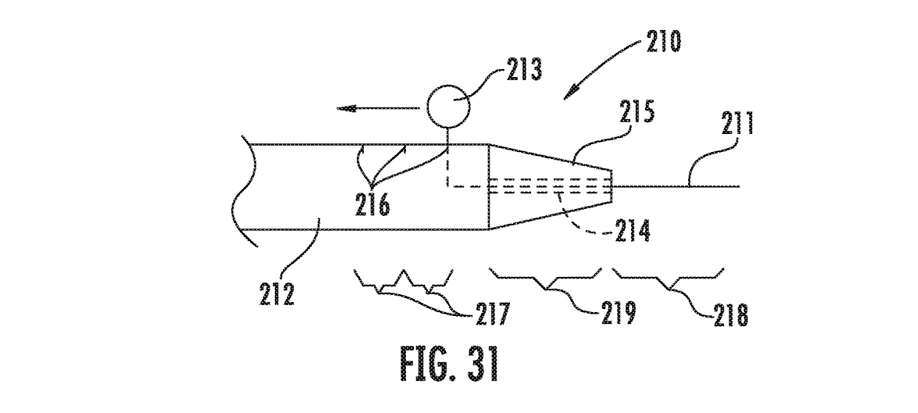
FIG. 31 is a partial schematic side view of a probe having distal end advanceable in fixed intervals, with hidden components shown in broken lines.

In a further embodiment (FIG. 31), a probe 210 has a distal end 211 that is displaceable relative to a body 212 of the probe 210. The distal end 211 is connected to an operator 213 and slidably supported in a channel 214 defined within a distal section 215 of the body 212. Using the operator 213, the distal end 211 is advanceable and retractable. Preferably, the detents 216 are formed in the body 212 to allow the distal end 211 to be advanced and retracted in fixed intervals 217. Advantageously, three detents 216 are formed with intervals 217 therebetween of approximately 2 mm, allowing the distal end 211 to be advanced to a maximum length 218 of approximately 6 mm. Preferably, the channel 214 supporting the distal end 211 has a length 219 at least equal to the maximum length 218. It will be appreciated that the probe 210 reduces the need for separate probes having differently dimensioned distal ends.

In an additional embodiment (FIG. 32), a probe 310 has a distal end 311 connected to a wire spool 312. Within a probe body 313, wire from the spool 312 is routed through a fixation element 314, which is rearwardly biased against a plunger 315 by a spring 316. The spring 316 is arranged in a cap 317 that is releasably connected, for instance by a threaded joint, to the body 313, allowing easier access to the wire.

Figure 32:
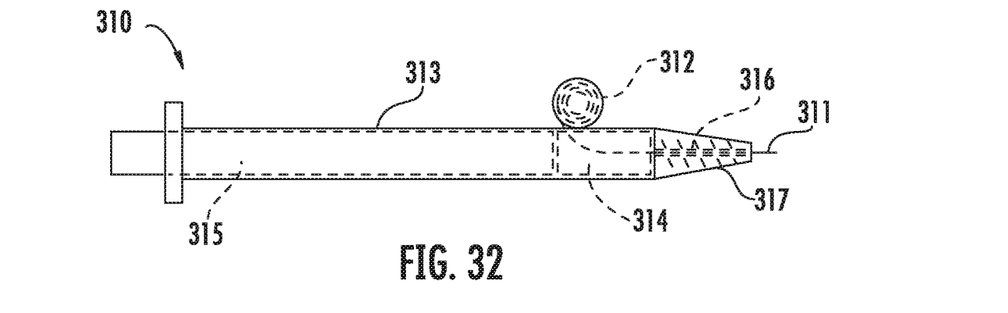
FIG. 32 is a schematic side view of a probe having a spool of wire advanceable to replace a damaged distal end and a plunger to advance the distal end, with hidden components shown in broken lines.

The distal end 311 is threaded through the fixation element 314 to the end of the cap 317 by feeding wire from the spool 312. A thumb wheel or other operation may advantageously be provided for the spool 312. The fed wire is secured within the fixation element 314. The plunger 315 is then operable to engage the fixation element 314 to advance the distal end 311 to a desired length. Preferably, the plunger 315 is operable in cooperation with the body 313 to advance the distal end 311 in fixed intervals. It will be appreciated that the probe 310 reduces the need to dispose of a probe when its distal end becomes bent or otherwise rendered unsuitable for continued use. Instead, the unsuitable portion can be cut off and the wire advanced to form a new distal end.

In the embodiment illustrated in FIGS. 2-4, 8, and 9, the probe 20 can have a longitudinal lumen 21 therethrough, with a plurality of distal holes 22 through the probe wall 23 in fluid communication with the lumen 21, as well as a tapered tip 24. The lumen 21 can be used in concert with a source of suction 25 (FIG. 9) for removing contents 26 from the meibomian gland 13, and/or with a source of a fluid and pumping means 27 (FIG. 8), for injecting a substance 28 into the meibomian gland 13. For probes having longitudinal lumens, polyimid tubes have been found satisfactory.

Figure 10:
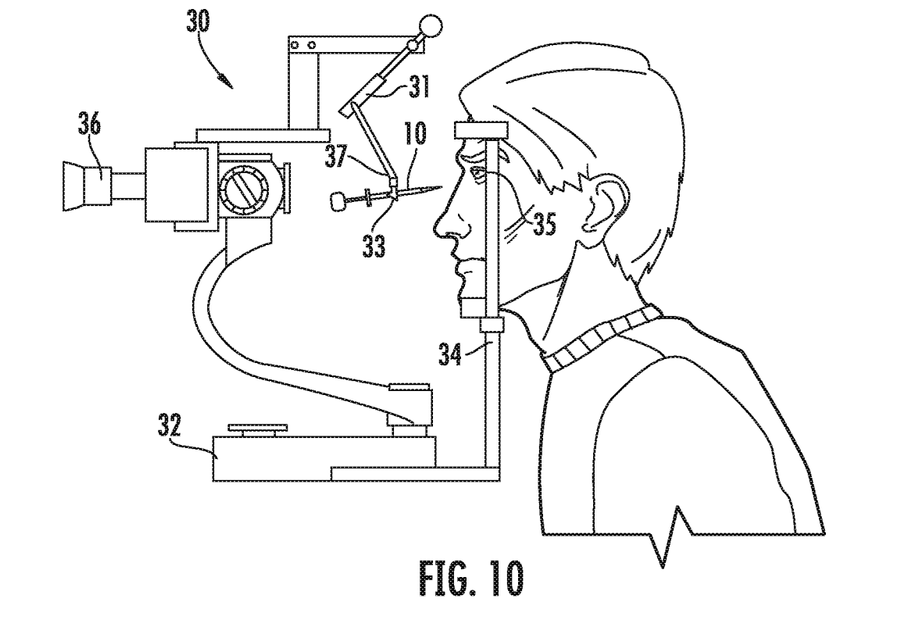
FIG. 10 is a side perspective view of an instrument for supporting a probe.

In order to provide stability to the probe 10, an apparatus may be contemplated for supporting the probe 10. For example, in the apparatus 30 illustrated in FIG. 10, an articulated arm 31 is affixed to a base 32, the arm 31 having a clamp 33 at a distal end 37 for releasably holding the probe 10. A patient head rest 34 retains the eye 35 in a stable position, and the physician can visualize the eyelid 35 and probe 10 through visualization optics, for example, a scope 36, which are positioned on an opposite side of the probe 10 from the patient eyelid 35.

Figure 11:
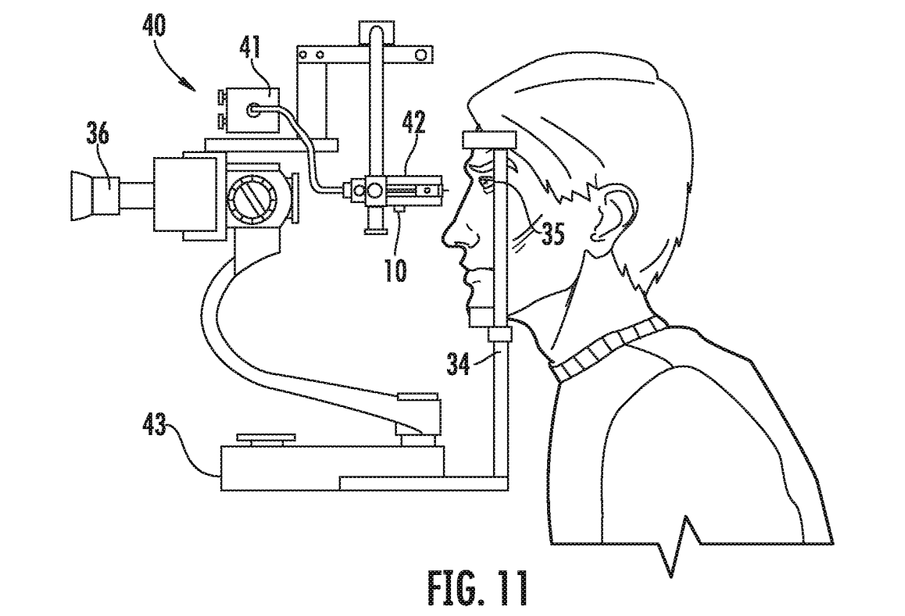
FIG. 11 is a side perspective view of an automated instrument for supporting and guiding a probe with a pump for aspiration and/or delivery.

In another apparatus 40 illustrated in FIG. 11, a motion-producing element such as a motor 41 driven automated support 42 is affixed to a base 43, and is controllable by a user. The motion imparted to the probe 10 is preferably substantially linear, and, once the user has ascertained that the probe tip 11 is aligned with the gland orifice 12, the motor 41 can be activated to impel the probe 10 into the meibomian gland 13. The other elements can be substantially the same as in FIG. 10.

Visualization can also be enhanced with the use of cross-illumination on the lower lid, for either manual insertion of the probe 10 or insertion using the apparatus 30 or 40. Cross-illumination of the lower lid can also aid in determining whether a given meibomian gland has atrophied, such there is, effectively, no gland to penetrate.

Figure 12:
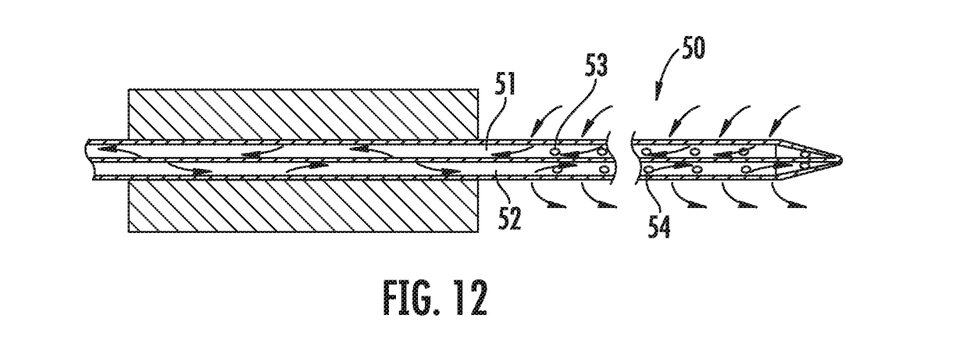
FIG. 12 is a side cross-sectional view of a probe having a double lumen for performing both aspiration and fluid delivery.

In another embodiment, a probe 50 (FIG. 12) includes a double lumen 51,52 running axially therealong. The first lumen 51 can be used for aspiration through a first distal hole 53 in fluid communication therewith, while the second lumen 52 can be used for injection of a fluid through a second distal hole 54 in fluid communication therewith.

Figure 13:
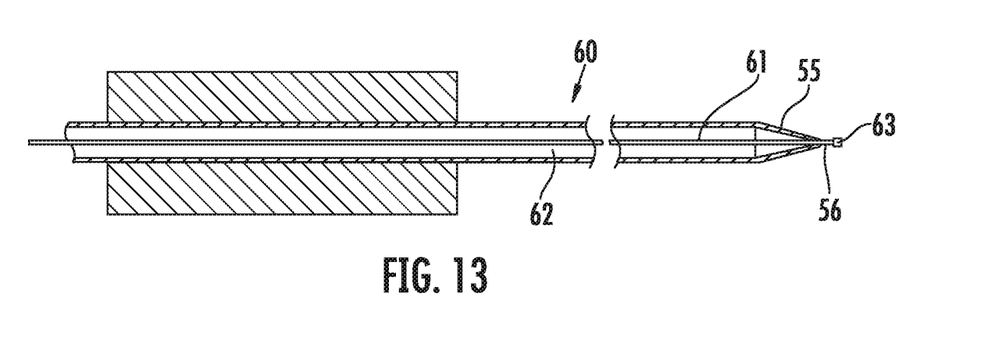
FIG. 13 is a side cross-sectional view of a probe having a movable element therein.
Figure 29:
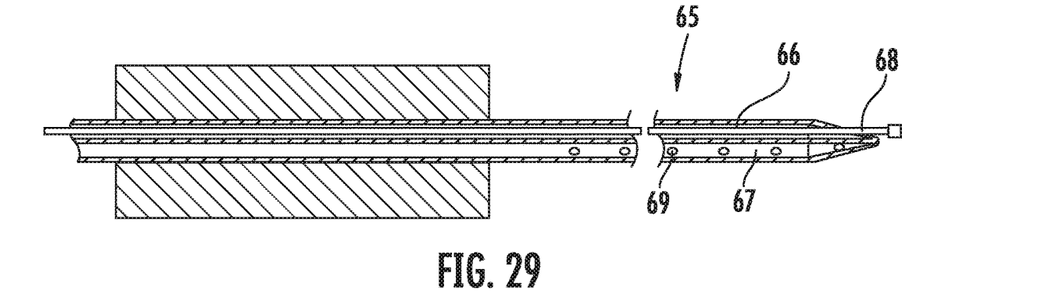
FIG. 29 is a side cross-sectional view of a probe having a double lumen and a movable element in one of the lumina.

A further embodiment 60 (FIG. 13) includes an elongated element 61 movable within the probe lumen 62 a distal section 56 of which is adapted to protrude out from the probe's distal end 55. The movable element 61 can have an enlarged tip 63 to assist in removing obstructions, which can protrude out from the probe distal end 55. In a similar embodiment, a probe 65 (FIG. 29) having a double lumen 66,67 can have a movable element 68 in one of the lumina 66, with the second lumen 67 having apertures 69 in communication therewith.

It may be contemplated by one of skill in the art that a plurality of probe tip embodiments may be encompassed by the present invention. The probe tip embodiments can comprise an obstruction-removing element useful for, for example, dislodging debris from the meibomian gland when the probe is moved therewithin.

Figure 14:
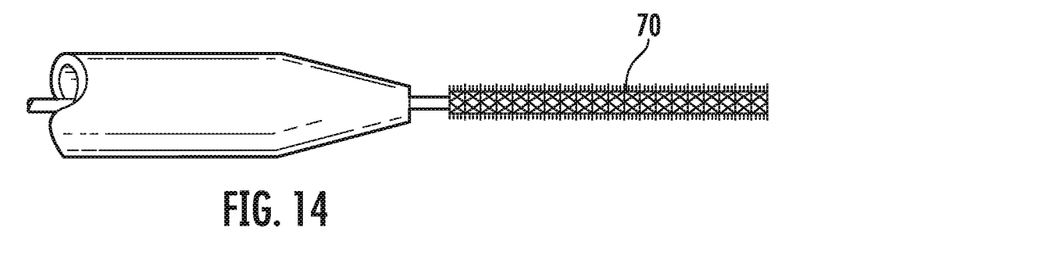
FIGS. 14-18 are side cross-sectional views of alternate embodiments of probe tips.
Figure 15:
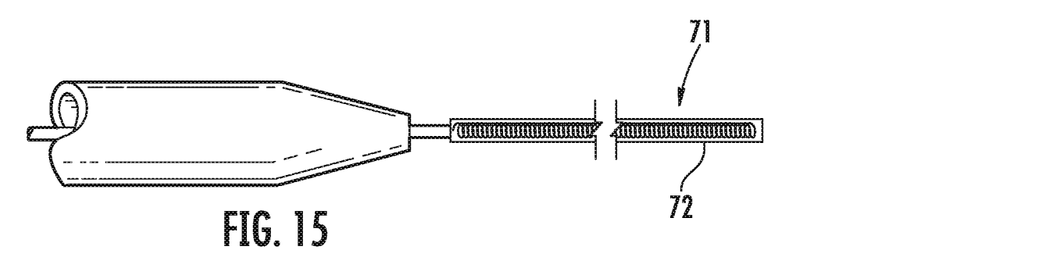
Figure 16:
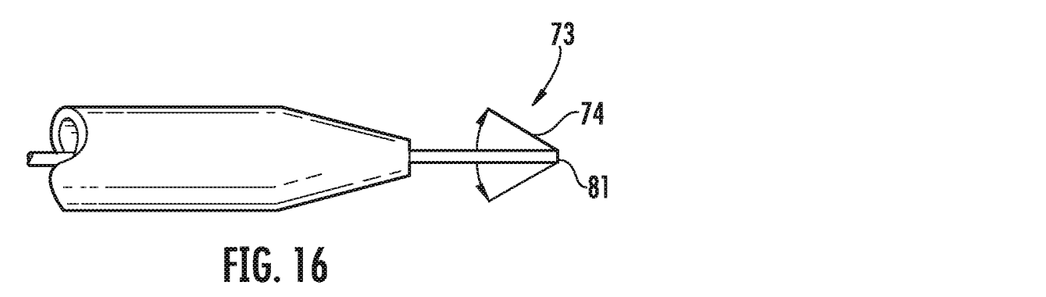
Figure 17:
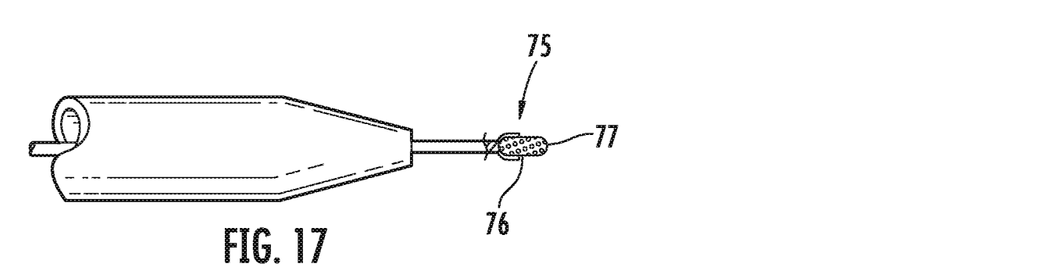
Figure 18:
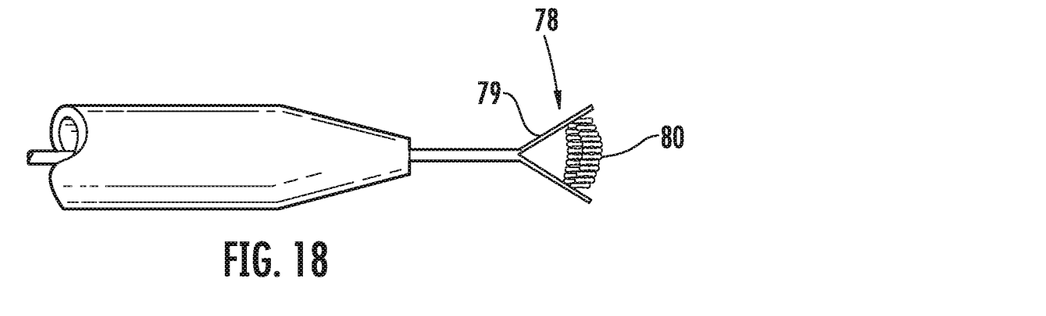

The probe tip embodiments can include, but are not intended to be limited to, an exfoliating tip 70 (FIG. 14), a tip 71 having a heating element 72 (FIG. 15), a tip 73 having a router 74 articulated at a distal end 81 (FIG. 16), a tip 75 having a gripper 76 for holding a releasing a medication-delivery element such as a pill 77 (FIG. 17), and a tip 78 having a gripper 79 for delivering a compressible, substantially toroidal stent 80 (FIG. 18). The stent may have drug eluting properties to deliver a pharmaceutical or other liquid therapy over time. In connection with some or all of these tips, particularly, the exfoliating and routing tips, a means for imparting vibratory motion can be coupled with the tip. Vibration at ultrasonic frequencies can also be employed.

Figure 19:
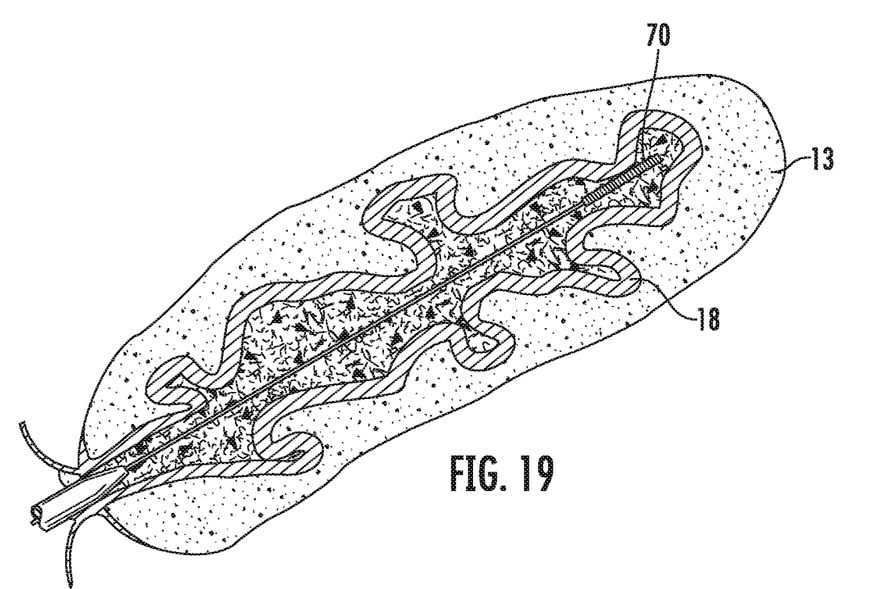
FIGS. 19 and 20 are side cross-sectional views of a meibomian gland illustrating the use of an exfoliating probe.
Figure 20:
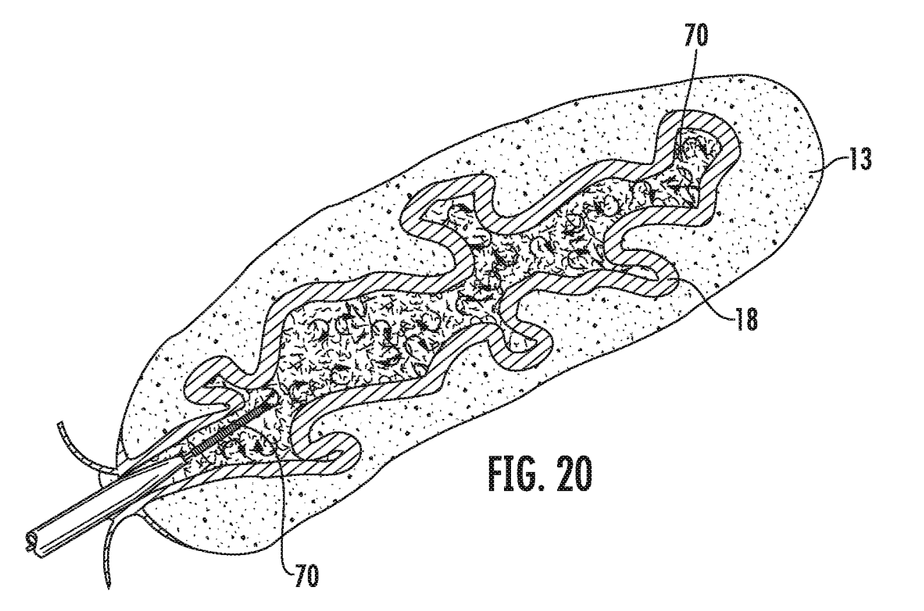
Figure 21:
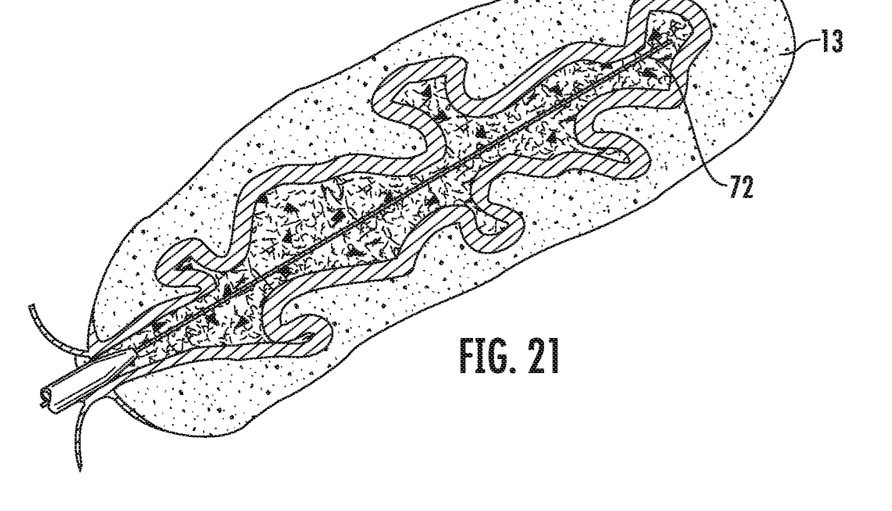
FIGS. 21 and 22 are side cross-sectional views of a meibomian gland illustrating the use of a heating element.
Figure 22:
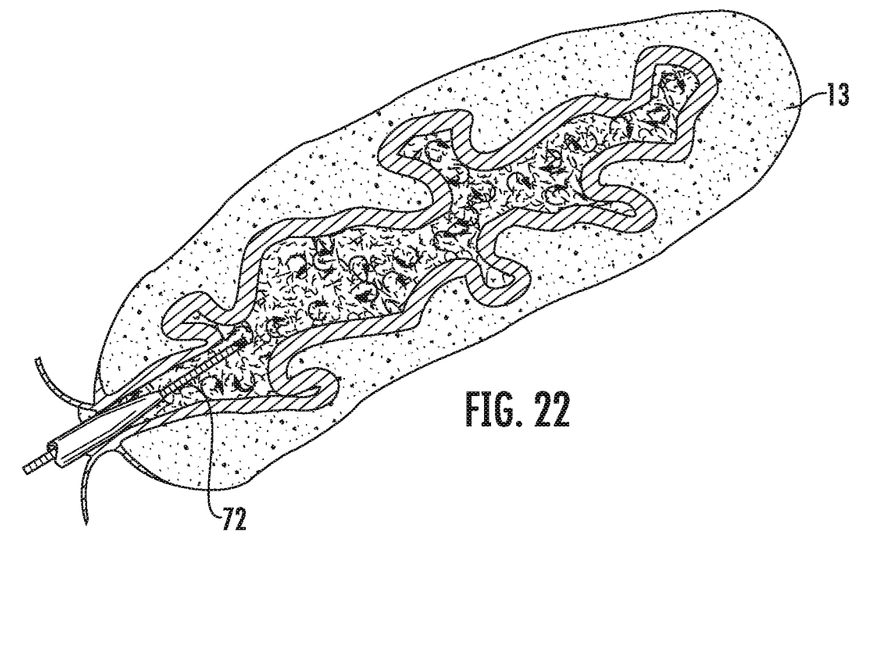
Figure 23:
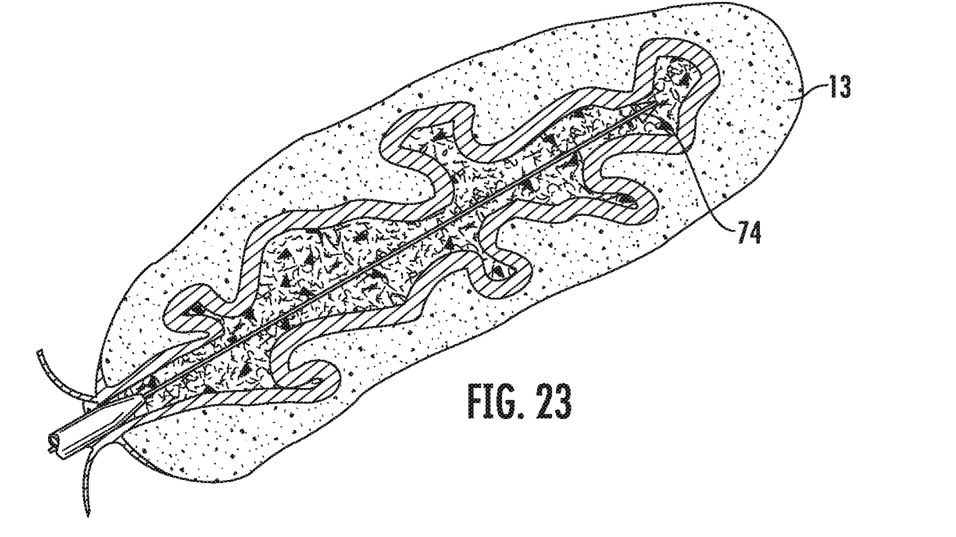
FIGS. 23 and 24 are side cross-sectional views of a meibomian gland illustrating the use of a "scoop"-type probe.
Figure 24:
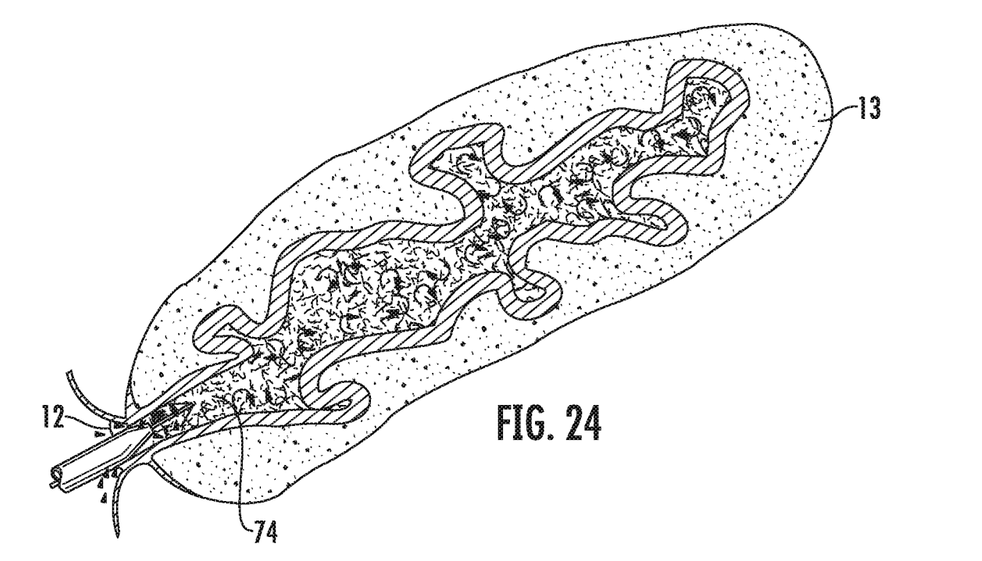
Figure 25:
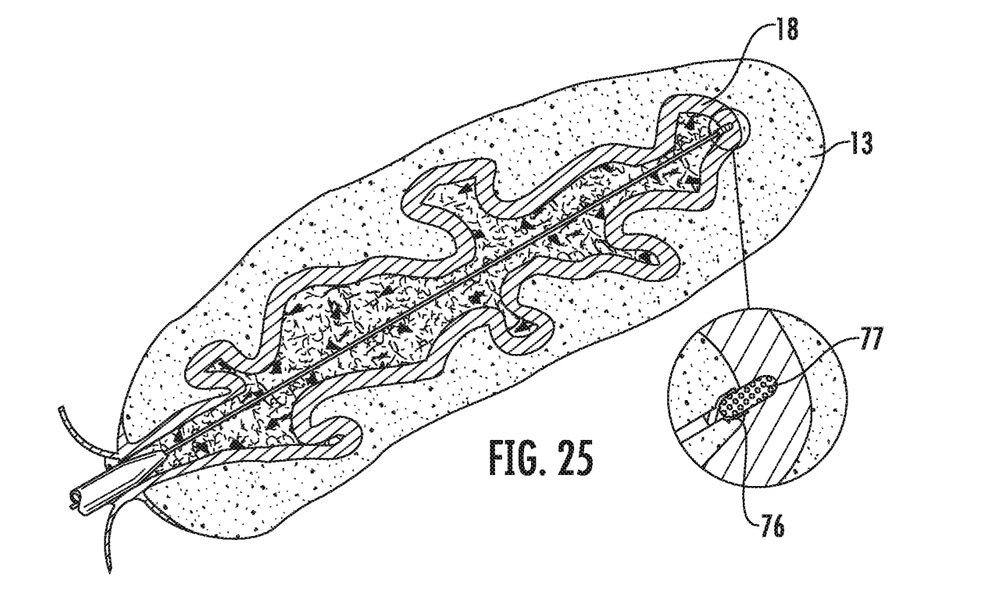
FIGS. 25 and 26 are side cross-sectional views of a meibomian gland illustrating the placement of a delivery element therein.
Figure 26:
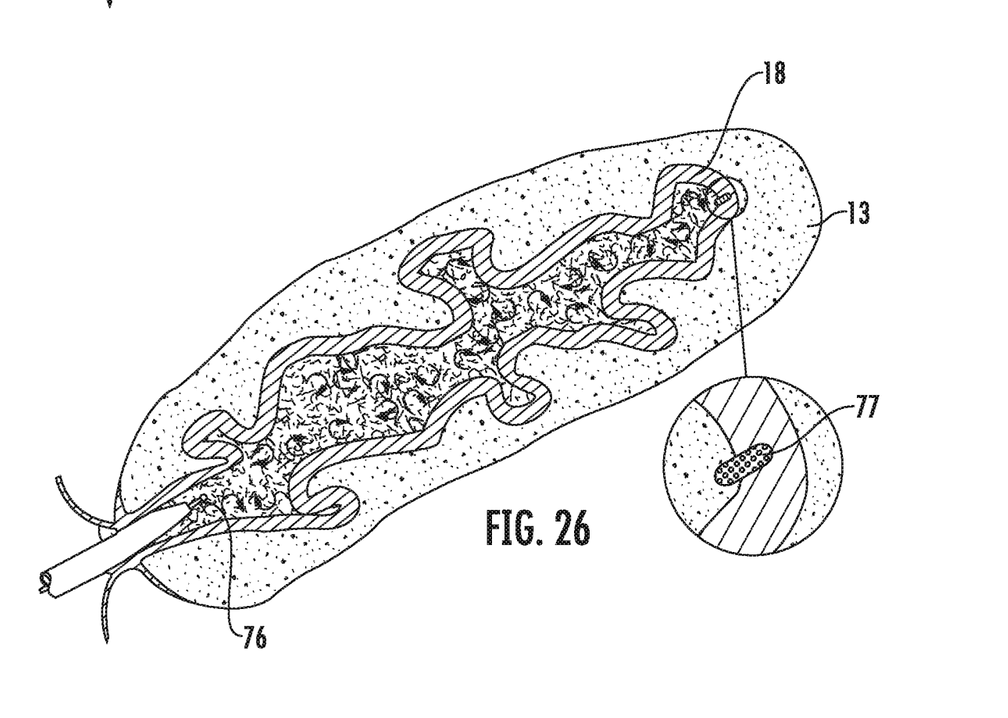
Figure 27:
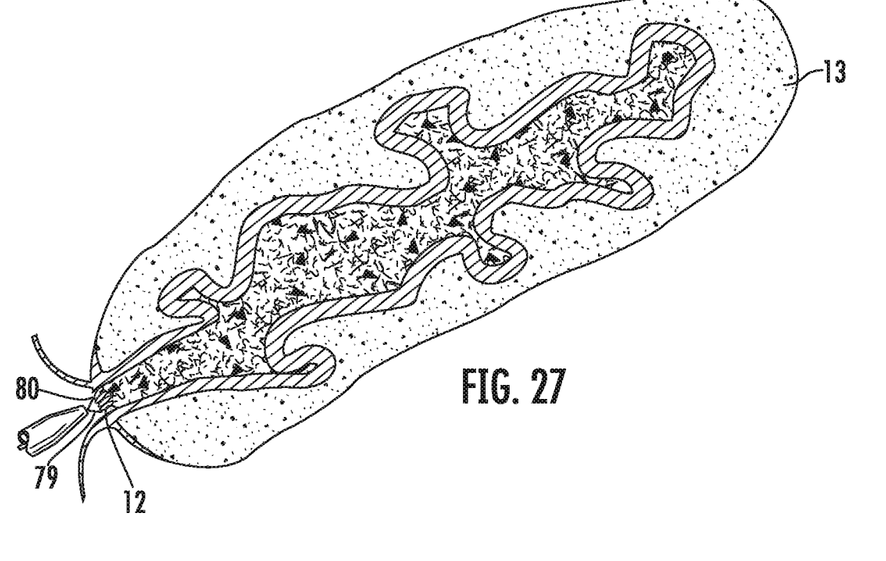
FIGS. 27 and 28 are side cross-sectional views of a meibomian gland illustrating the use of a stent-delivery probe.
Figure 28:
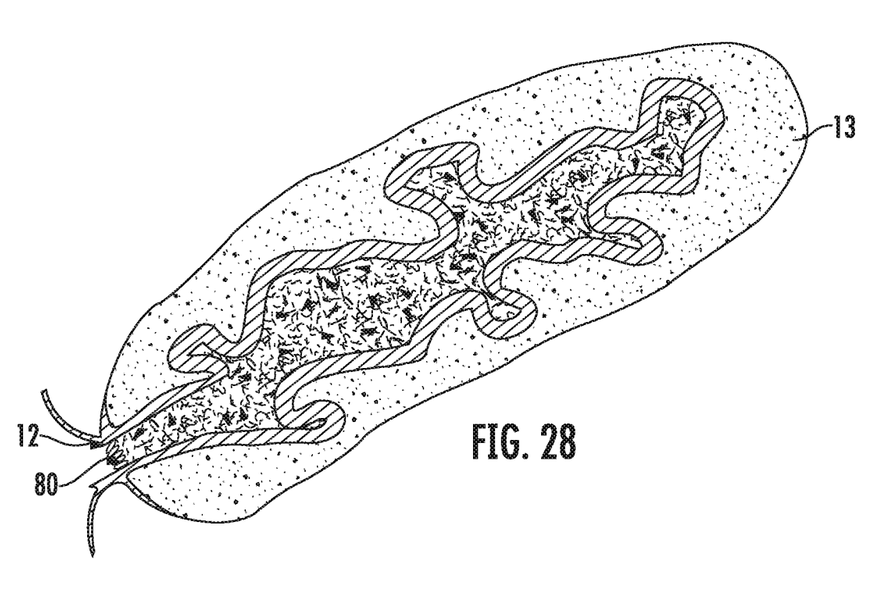

The uses of these tips are illustrated in FIGS. 19-28. In FIGS. 19 and 20, the exfoliating tip 70 is shown loosening material from the gland wall 18; in FIGS. 21 and 22, the heating element 72 is used to release contents by reducing fluid viscosity; in FIGS. 23 and 24, the router 74 is expanded to scrape debris out the orifice 12; in FIGS. 25 and 26, the gripper tip 76 is used to deliver a pill 77 to the gland wall 18, which can contain such materials as, but not intended to be limited to, medication, stem cells, solvents, growth factors, nutrients, vitamins, hormones, genetic vectors, a nanotechnological element, or a radioactive substance for treating sebaceous cell or other type of cancer. In FIGS. 27 and 28, the stent-delivery tip 79 is illustrating as holding the stent 80 in a compressed condition and leaving in place the stent 80, which will expand for assisting in keeping the orifice 12 in an open position. Although, the depicted stent 80 is substantially confined to the orifice 12, the present invention can also include stents that extend from the orifice into the gland or duct for all, or a portion of, its length. Stents located within the duct or gland but not extending in to the orifice can also be used.

It can be seen that the various embodiments of probes disclosed herein are useful for a plurality of purposes, including those outlined above and diagnostic cytology, brachytherapy, and light-activated fluorescence for treating cancer.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction or use.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A device for treating a gland or duct of a patient comprising:
    a probe having an elongated distal end with an outer diameter of approximately 150 μm or less and a length of approximately 6 mm or less; and
        a structural support positionable by the device within the gland or duct adjacent a natural orifice thereinto, for assisting the retaining the orifice in an unobstructed condition, the structural support being detachable from the device for retention in the orifice after removal of the probe;
    wherein the probe has a longitudinal lumen extending therealong defined by a probe wall and a distal hole through the probe wall in fluid communication with the lumen, the distal hole positioned in the probe distal end.

2. The device recited in claim 1, wherein the structural support comprises a compressible, substantially toroidal element, and a gripper operable to releasably hold the toroidal element in a compressed condition is extendable from within the longitudinal lumen through the distal hole, a release of the toroidal element from the gripper permitting the toroidal element to expand and assist in holding the orifice open.

3. The device recited in claim 1, wherein the elongated distal end is stainless steel.

4. A device for treating a gland or duct of a patient comprising:
    a probe having an elongated distal end with an outer diameter of approximately 150 μm or less and a length of approximately 6 mm or less;
    wherein the probe has an obstruction-removing element adjacent the probe distal end adapted for dislodging debris from the gland or duct; and
    wherein the obstruction-removing element comprises a router articulated at a distal end, such that, upon inserting the probe distal end, the router is able to be opened and moved in a proximal direction for scraping the gland or duct.

5. The device recited in claim 4, wherein the elongated distal end is stainless steel.

* * * * *